(12) United States Patent
Welzig et al.

(10) Patent No.: US 10,143,751 B2
(45) Date of Patent: *Dec. 4, 2018

(54) PHOTODYNAMIC THERAPY, FORMULATION USABLE FOR THIS PURPOSE, AND METHOD FOR THE PRODUCTION AND USE THEREOF

(71) Applicant: Sanochemia Pharmazeutika AG, Vienna (AT)

(72) Inventors: Stefan Welzig, Vienna (AT); Gregor Medinger, Sag Harbor, NY (US); Beate Kalz, Steinbrunn (AT); Jozsef Gungl, Agfalva (HU); Klaus Gerdes, Dusseldorf (DE); Werner Frantsits, Vienna (AT); Christina Abrahamsberg, Vienna (AT)

(73) Assignee: SANOCHEMIA PHARMAZEUTIKA AG, Vienna (AT)

( * ) Notice: Subject to any disclaimer, the term of this patent is extended or adjusted under 35 U.S.C. 154(b) by 330 days.

This patent is subject to a terminal disclaimer.

(21) Appl. No.: 14/878,515

(22) Filed: Oct. 8, 2015

(65) Prior Publication Data

US 2017/0087249 A1    Mar. 30, 2017

(30) Foreign Application Priority Data

Sep. 28, 2015 (AT) .................. A 630/2015

(51) Int. Cl.
*A61K 41/00* (2006.01)
*A61K 47/58* (2017.01)
*A61K 47/60* (2017.01)
*A61K 9/00* (2006.01)
*A61K 9/08* (2006.01)
*A61K 9/19* (2006.01)
*A61K 47/32* (2006.01)
*A61N 5/06* (2006.01)

(52) U.S. Cl.
CPC ........ *A61K 41/0057* (2013.01); *A61K 9/0009* (2013.01); *A61K 9/08* (2013.01); *A61K 9/19* (2013.01); *A61K 47/32* (2013.01); *A61K 47/58* (2017.08); *A61K 47/60* (2017.08); *A61N 5/062* (2013.01); *A61N 2005/0663* (2013.01)

(58) Field of Classification Search
CPC .................................. A61K 41/0057
See application file for complete search history.

(56) References Cited

U.S. PATENT DOCUMENTS 6,472,439 B1   10/2002   Schierstedt
7,390,510 B2   6/2008    Kubin et al.

FOREIGN PATENT DOCUMENTS

| DE | 19756677 | 6/1999 |
|---|---|---|
| DE | 19756677 A1 | 6/1999 |
| DE | 102014204138 A1 | 9/2015 |
| EP | 1289562 B1 | 3/2003 |
| WO | 2009/0066294 | 5/2009 |
| WO | 2009/0066294 A1 | 5/2009 |
| WO | 2015/131891 | 9/2015 |
| WO | 2015/131891 A1 | 9/2015 |

OTHER PUBLICATIONS

Huygens, et al. "Stability of different formulations and ion pairs of hypericin," European Journal of Pharmaceutics and Biopharmaceutics, vol. 59, Issue 3, Apr. 2005, Abstract only.

Austrian Search Report for corresponding Austrian Application No. A 630/2015, dated Apr. 13, 2016.

Huygens, et al. "Stability of different formulations and ion pairs of hypericin," European Journal of Pharmaceutics and Biopharmaceutics, vol. 59, Issue 3, Apr. 2005, pp. 461-464, Abstract only.

*Primary Examiner* — Kortney L. Klinkel
*Assistant Examiner* — Tori Strong
(74) *Attorney, Agent, or Firm* — Young & Thompson

(57) ABSTRACT

Photodynamic therapy of tumors such as bladder tumors includes photosensitizing with a photosensitizer that is a complex or a compound of hypericin and a polymeric complexing agent. The photosensitizer is formed from an alkali salt of hypericin and the polymeric complexing agent. The alkali salt of hypericin is a sodium salt or a potassium salt. The complexing agent is a polyethylene glycol or a poly-N-vinyl amide.

20 Claims, 1 Drawing Sheet

PHOTODYNAMIC THERAPY, FORMULATION USABLE FOR THIS PURPOSE, AND METHOD FOR THE PRODUCTION AND USE THEREOF

FIELD OF THE INVENTION

The invention relates to a method for photodynamic therapy, a formulation of hypericin, which can be used in photodynamic therapy, a method for the production, and the use thereof for the production of a photosensitizer.

BACKGROUND OF THE INVENTION

The photodynamic therapy (PDT) is a method that is suitable for treating tumors and premalignant changes in the skin and mucosa of various hollow organs (Juarranz et al., 2008; Agostinis et al., 2011).

The PDT is based on the interaction of three components: photosensitizer, light in the visible range, and oxygen.

After systemic or topical application of a photosensitizer, an accumulation of the photosensitizer is carried out in the malignant tissue. Using light of a suitable wavelength, the photosensitizer can be stimulated. In the stimulated state, energy is transferred to a reactant, e.g., molecular oxygen. In this case, reactive oxygen molecules are generated, which in turn damage cellular structures of the tumor tissue, by which cellular processes such as apoptosis and necrosis are introduced (Agostinis, et al., 2011; Allison and Sibata, 2010).

A more ideal photosensitizer for the PDT shows selective accumulation in tumor cells, no or minimal systemic toxicity, and it is photochemically efficient.

Hypericin 1,3,4,6,8,13-hexahydroxy-10, 11-dimethyl-phenanthro (1,10,9,8-opqra)perylene-7, 14-dione was already described as a potential photosensitizer in the literature (Agostinis et al., 2002).

In in-vitro studies, the effectiveness of hypericin in PDT was shown in a series of cell lines (Karioti and Bilia, 2010).

Moreover, in-vivo animal studies confirm the potential of hypericin for application in PDT (Bhuvaneswari et al., 2010; Chen et al., 2003; Liu et al., 2000; Sanovic et al., 2011).

Hypericin is hydrophobic and water-insoluble. For this reason, in the past, hypericin was brought into solution using the organic solvent dimethyl sulfoxide (DMSO) or a water-soluble polymer, polyethylene glycol (PEG).

Animal experiments in a rat model showed encouraging results with respect to the PDT of bladder carcinoma. In this case, hypericin was brought into the tumor cells using polyethylene glycol. With a hypericin dose of 30 μM and an irradiation with light (595 nm) of an intensity of 25 up to 50 mW/cm$^2$, up to 98% of the tumor cells were killed (Kamuhabwa et al. 2003).

For a clinical application, however, a water-soluble formulation of hypericin is required, which has tumor selectivity and can be stimulated with light in the visible range.

The document WO 01/89576 A2 describes how the solubility of hypericin can be increased by the adjuvant polyvinylpyrrolidone (povidone, PVP).

The use of PVP-hypericin in PDT is also described in WO 2014/079972 A1. WO 2014/079972 A1 deals with in particular a device that can be used in the PDT of hollow organs, such as the human bladder.

PVP-hypericin shows a selective accumulation in tumor cells in vitro and in vivo (Kubin et al., 2008; Vandepitte et al., 2011).

SUMMARY OF THE INVENTION

As a first object, the invention is based on making available an improved method for photodynamic therapy.

This object is achieved with a method for photodynamic therapy of tumors, in which as a photosensitizer, a complex or a compound that consists of hypericin and a polymeric complexing agent is used and in which as a photosensitizer, a complex or a compound that consists of an alkali salt of hypericin and a polymeric complexing agent is used.

The object of the invention is also to make available a sterile and stable formulation of hypericin, which can be used for clinical application in photodynamic therapy (PDT).

This object is achieved with a formulation that contains hypericin that is bonded or complexed to a polymeric complexing agent, whereby hypericin is present as a salt.

The object of the invention is also to make available a method for the production of a formulation of hypericin that can be used in a photodynamic therapy as a photosensitizer.

This object is achieved with a method in which hypericin salt is bonded or complexed to a polyethylene glycol or to a poly-N-vinyl amide, preferably polyvinylpyrrolidone (PVP).

Moreover, the invention is based on an advantageous use of the formulation according to the invention.

In this respect, the invention relates to the use of the formulation according to the invention for the production of a photosensitizer that can be used in photophysical or photodynamic therapy.

Preferred and advantageous embodiments of the therapy according to the invention, the formulation according to the invention, the method for the production, and the use thereof are subjects of the subclaims.

DETAILED DESCRIPTION OF THE INVENTION

Figure 1:
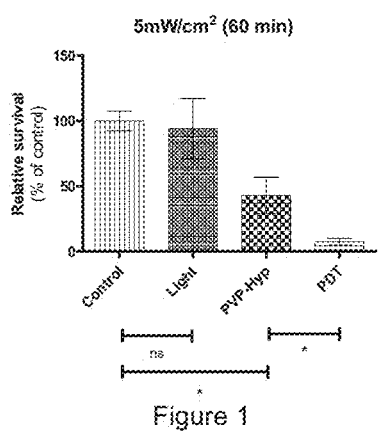
FIGS. 1 and 2 depict the survival of tumor cells after treatment with the hypericin formulation of the invention at a light intensity of 5 and 25 mW/cm$^2$.
Figure 2:
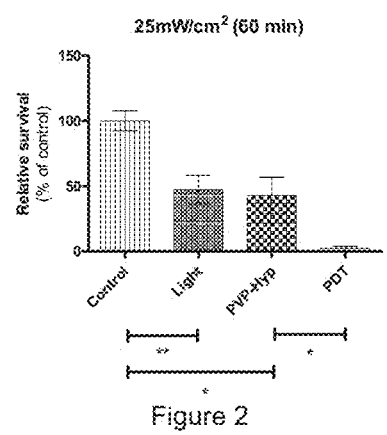

Surprisingly enough, it has been shown that the formulation of hypericin according to the invention can be applied in a stable manner and thus under clinical conditions in the therapy according to the invention only when hypericin is present as a salt.

An evaluation of the therapy according to the invention with use of the formulation of hypericin according to the invention in animal experiments has shown, surprisingly enough, that in the case of a dose of 30 μM of hypericin in a stable formulation with PVP according to Example 1, a required light intensity of 5 or 25 mW/cm$^2$ at a wavelength of 595 nm and a 120-minute exposure time in the bladder (instillation time) is sufficient to kill 98% of the tumor cells. The same result of 98% killed tumor cells is also achieved at the same light intensity and 40 μM of hypericin at a 15- or 30-minute exposure time and treatment with light of a wavelength of 610 nm. Also, an instillation time of 1 hour, with 20 μM of hypericin, equal light intensity, and 570 nm of light frequency, achieves a kill rate of 97%, and an instillation time of 120 minutes, with 9 μM of hypericin, equal light intensity, and treatment at 600 nm, achieves a kill rate of 95%. Thus, in the case of light intensities of 5 to 25 mW/cm$^2$ with light frequencies of 570 to 610 nm, hypericin concentrations of 9 to 40 μM, and exposure times of between 15 and 120 minutes, a kill rate of 95 to 98% of the tumor cells (Practical Examples 1, 2, 3, and 4) is achieved.

The effectiveness of a PDT is essentially dependent upon the total amount of light. At the same time, the probability of local side effects is increased with increasing light intensity.

Using therapy according to the invention, in particular with use of the formulation according to the invention, an improved accumulation in malignant tissue is achieved, by which a considerably reduced light intensity of already 5 to at most 25 mW/cm$^2$ is sufficient in order to kill tumor cells.

The selective concentration of the formulation of hypericin according to the invention and the surprisingly low light intensity, which was required for a PDT in the animal model during application of the formulation of hypericin according to the invention, allows the application in the treatment of lesions in various cavities of the body that can be reached with the necessary light dose.

Below, examples of the formulation of hypericin (hypericin-PVP complex) according to the invention are presented.

General procedure for the production of a formulation with the active ingredient sodium hypericinate:

The goal is the production of a hypericin-containing formulation for application as a photosensitizer in the field of photodynamic therapy.

The formulation according to the invention is produced from a hypericin salt, in particular from sodium hypericinate.

In order to define the hypericin content of the starting material, in addition to the determination of contents, primarily water content and, in the case of sodium hypericinate, the proportion of sodium are specified.

The chemical-physical properties can have an influence on the formulation of the pharmaceutical agent.

For the clinical application, a stability of the formulation according to the invention is necessary. The stability is ensured through the composition of the finished product and at the same time also relates to the production method. Because of the buffer systems used, adequate stability of the bulk solution can also be achieved during production until lyophilization of the finished product takes place.

As buffer systems, various additives can be used, which preferably both for the bulk solution and for the reconstituted solution achieve a physiologically compatible pH and an osmotic pressure of 290 mOsmol/kg after reconstitution with 50 ml of water for injection. Phosphate or citrate buffer systems can be used primarily.

After the bulk solution is made up from the above-mentioned components, the corresponding amount of the bulk solution is decanted into injection flasks and freeze-dried.

Example 1

From sodium hypericinate, a solution with a target weighed-in amount of 90.0 mg of hypericin is produced.

5.0 g of the hypericin solution is added to 1,875 mg of PVP k25 and completely dissolved.

This solution is quantitatively made up to 250.0 g with a phosphate buffer solution. The final concentration of this solution is 0.0225 mg of hypericin/g of solution.

For lyophilization, a defined amount of the thus obtained bulk solution is decanted into injection flasks, and the finished lyophilizate is produced with a corresponding lyo program.

Example 2

The procedure is the same as indicated in Example 1, whereby instead of PVP k25, PVP k17 is used for complexing sodium hypericinate.

Example 3

The procedure is the same as indicated in Example 1, whereby instead of PVP k25, PVP k30 is used for complexing sodium hypericinate.

Example 4

The procedure is the same as indicated in Examples 1, 2, or 3, whereby instead of the phosphate buffer solution, a citric acid buffer solution is used.

The bulk solutions that are produced as described in Examples 1 to 4 can be produced with different hypericin contents.

The effectiveness of the therapy according to the invention with use of the formulation of hypericin according to the invention was examined in a preclinical study with use of the formulation as Example 1.

Practical Examples

To this end, the formulation of hypericin according to the invention for the PDT was studied in a preclinical, orthotopic bladder tumor model in rats. In all examples, the tumors were treated with the formulation of hypericin according to the invention in different concentrations of 9 to 40 µM, with different light intensities of 5 or 25 mW/cm$^2$, different light frequencies of 570 to 610 nm, and different instillation times.

Example 1

After a 2-hour instillation with 30 µM of the formulation of hypericin according to the invention and different light intensities (5 or 25 mW/cm$^2$) with light of a wavelength of 595 nm, up to 98% of the tumor cells were killed.

Example 2

After a 1-hour instillation with 20 µM of the formulation of hypericin according to the invention and different light intensities (5 or 25 mW/cm$^2$) with light of a wavelength of 570 nm, up to 97% of the tumor cells were killed.

Example 3

After a 15- or 30-minute instillation with 40 µM of the formulation of hypericin according to the invention and different light intensities (5 or 25 mW/cm$^2$) with light of a wavelength of 610 nm, up to 98% of the tumor cells were killed.

Example 4

After a 2-hour instillation with 9 µM of the formulation of hypericin according to the invention and different light intensities (5-25 mW/cm$^2$) with light of a wavelength of 600 nm, up to 95% of the tumor cells were killed.

The results of the studies on the rat model are presented in the figure. In the diagrams, "ns" stands for "not significant," and "*" stands for "significant." The diagrams of the figure show the survival of tumor cells after treatment with the formulation of hypericin according to the invention and light. 24 hours after the treatment, the bladder tissue was dissociated, and the surviving cells were determined using a clonogenic assay in comparison to the control (without PVP-hypericin and light).

The relative survival of the cells under PDT conditions (PVP-hypericin according to Example 1 and treatment with light) is (depicted as mean value+SD): 7.4 (+/−6.4)% with use of 5 mW/cm$^2$ and 2.4 (+/−4.0)% at 25 mW/cm$^2$ and a treatment period with light of 60 minutes. This is depicted in two diagrams in the figure.

REFERENCES

Agostinis, P.; Berg, K.; Cengel, K. A.; Foster, T. H.; Girotti, A. W.; Gollnick, S. O.; Hahn, S. M.; Hamblin, M. R.; Juzeniene, A.; Kessel, D.; Korbelik, M.; Moan, J.; Mroz, P.; Nowis, D.; Piette, J.; Wilson, B. C.; Golab, J. Photodynamic Therapy of Cancer: An Update. CA Cancer J Clin. 2011 July-August; 61(4): 250-281

Agostinis P.; Vantieghem, A.; Merlevede, W.; de Witte, P. A. Hypericin in Cancer Treatment: More Light on the Way. Int J Biochem Cell Biol. 2002 March; 34(3): 221-241

Allison, R. R.; Sibata, C. H. Oncologic Photodynamic Therapy Photosensitizers: A Clinical Review. Photodiagnosis Photodyn Ther. 2010 June; 7(2): 61-75

Bhuvaneswari, R.; Thong, P. S.; Gan, Y. Y.; Soo, K. C.; Olivo, M. Evaluation of Hypericin-Mediated Photodynamic Therapy in Combination with Angiogenesis Inhibitor Bevacizumab Using In Vivo Fluorescence Confocal Endomicroscopy. J Biomed Opt. 2010 January-February; 15(1): 011114. Erratum in: J Biomed Opt. 2010

Chen, B.; Ahmed, B.; Landuyt, W.; Ni, Y.; Gaspar, R.; Roskams, T; de Witte, P. A. Potentiation of Photodynamic Therapy with Hypericin by Mitomycin C in the Radiation-Induced Fibrosarcoma-1 Mouse Tumor Model. Photochem Photobiol. 2003 September; 78(3): 278-282.

Juarranz, A.; Jaén, P.; Sanz-Rodríguez, F.; Cuevas, J.; González, S. Photodynamic Therapy of Cancer. Basic Principles and Applications. Clin Transl Oncol. 2008 March; 10(3): 148-154

Karioti, A.; Bilia, A. R. Hypericins as Potential Leads for New Therapeutics. Int J Mol Sci. 2010 Feb. 4; 11(2): 562-594

Kubin, A.; Meissner, P.; Wierrani, F.; Burner, U.; Bodenteich, A.; Pytel, A.; Schmeller, N. Fluorescence Diagnosis of Bladder Cancer with New Water Soluble Hypericin Bound to Polyvinylpyrrolidone: PVP-Hypericin. Photochem Photobiol. 2008; 84(6): 1560-1563

Kamuhabwa, A. A.; Roskams, T.; D'Hallewin, M. A.; Baert, L.; Van Poppel, H.; de Witte, P. A. Whole Bladder Wall Photodynamic Therapy of Transitional Cell Carcinoma Rat Bladder Tumors Using Intravesically Administered Hypericin. Int J Cancer. 2003 Nov. 10; 107(3): 460-467

Liu, C. D.; Kwan, D.; Saxton, R. E.; McFadden, D. W. Hypericin and Photodynamic Therapy Decreases Human Pancreatic Cancer In Vitro and in Vivo. J Surg Res. 2000 September; 93(1): 137-143

Sanovic, R. I.; Verwanger, T.; Hartl, A.; Krammer, B. Low Dose Hypericin-PDT Induces Complete Tumor Regression in BALB/c Mice Bearing CT26 Colon Carcinoma. Photodiagnosis Photodyn Ther. 2011 December; 8(4): 291-296

Vandepitte, J.; Van Cleynenbreugel, B.; Hettinger, K.; Van Poppel, H.; de Witte, P. A. Biodistribution of PVP-Hypericin and Hexaminolevulinate-Induced PpIX in Normal and Orthotopic Tumor-Bearing Rat Urinary Bladder. Cancer Chemother Pharmacol. Cancer Chemother Pharmacol. 2011 April; 67(4): 775-781

Vandepitte, J.; Roelants, M.; Van Cleynenbreugel, B.; Hettinger, K.; Lerut, E.; Van Poppel, H.; de Witte, P. A. Biodistribution and Photodynamic Effects of Polyvinylpyrrolidone-Hypericin Using Multicellular Spheroids Composed of Normal Human Urothelial and T24 Transitional Cell Carcinoma Cells. J. Biomed Opt. 2011 January-February; 16(1): 018001

The invention claimed is:

1. A method for photodynamic therapy of tumors, comprising:
   photosensitizing with a photosensitizer that is a lyophilizate obtained from a stable complex or a stable compound of an alkali salt of hypericin and a polymeric complexing agent in a buffer system of a phosphate buffer or a citric acid buffer,
   wherein the photosensitizer contains 0.225 mg of hypericin.

2. The method according to claim 1, wherein the alkali salt of hypericin is a sodium salt or a potassium salt.

3. The method according to claim 2, wherein a photodynamic therapy of bladder cancer is made.

4. The method according to claim 2, wherein the photosensitizer has a concentration of of 9 to 40 µM of hypericin, and the method further comprises applying light at light intensities of 5 to 25 mW/cm$^2$ at wavelengths of visible light in a yellow, orange and/or red spectral range.

5. The method according to claim 1, wherein the photosensitizer has a concentration of 9 to 40 µM of hypericin.

6. The method according to claim 1, further comprising:
   applying light at an intensity of of 5 to 25 mW/cm$^2$ at wavelengths of visible light in a yellow, orange and/or red spectral range.

7. The method according to claim 1, further comprising instillation times of 15 to 120 minutes.

8. The method according to claim 1, wherein the complexing agent is a polyethylene glycol or a poly-N-vinyl amide.

9. The method according to claim 8, wherein poly-N-vinyl amide is a polyvinylpyrrolidone (PVP) of various degrees of polymerization and cross-linking.

10. The method according to claim 9, wherein the polyvinylpyrrolidone is PVP k17, PVP k25 or PVP k30.

11. A method for photodynamic therapy of cancer or bladder cancer, comprising:
   photosensitizing with a photosensitizer that is a lyophilizate obtained from a stable complex or a stable compound of an alkali salt of hypericin and a polymeric complexing agent in a buffer system of a phosphate buffer or a citric acid buffer,
   wherein the photosensitizer contains 0.225 mg of hypericin.

12. A method for photodynamic therapy of tumors, comprising:
   photosensitizing with a photosensitizer that is a stable complex or a stable compound of a sodium or potassium salt of hypericin and a polymeric complexing agent selected from the group consisting of polyethylene glycol and poly-N-vinyl amide, wherein the photosensitizer is obtained from a lyophilisate obtained from a solution of the sodium or potassium salt of hypericin, containing 0.0225 mg hypericin/g solution, the polymeric complexing agent and a buffer system comprising a phosphate buffer or a citric acid buffer, wherein the solution has been lyophilized to obtain the photosensitizer containing 0.225 mg of hypericin.

13. The method according to claim 12, wherein the photosensitizer has a concentration of 9 to 40 µM of hypericin.

14. The method according to claim 12, further comprising:
applying light at an intensity of 5 to 25 mW/cm$^2$ at wavelengths of the visible light in a yellow, orange and/or red spectral range.

15. The method according to claim 12, further comprising instillation times of 15 to 120 minutes.

16. The method according to claim 12, wherein poly-N-vinyl amide is a polyvinylpyrrolidone (PVP) of various degrees of polymerization and cross-linking.

17. The method according to claim 16, wherein the polyvinylpyrrolidone is PVP k17, PVP k25 or PVP k30.

18. The method according to claim 12, wherein a photodynamic therapy of bladder cancer is made.

19. The method according to claim 12, wherein the photosensitizer has a concentration of of 9 to 40 µM of hypericin, and the method further comprises applying light at light intensities of 5 to 25 mW/cm$^2$ at wavelengths of visible light in a yellow, orange and/or red spectral range.

20. A method for photodynamic therapy of cancer, comprising:
photosensitizing with a photosensitizer that is a stable complex or a stable compound of a sodium or potassium salt of hypericin and a polymeric complexing agent selected from the group consisting of polyethylene glycol and poly-N-vinyl amide, wherein the photosensitizer is obtained from a lyophilisate obtained from a solution of the sodium or potassium salt of hypericin, containing 0.0225 mg hypericin/g solution, the polymeric complexing agent and a buffer system comprising a phosphate buffer or a citric acid buffer,
wherein the solution has been lyophilized to obtain the photosensitizer containing 0.225 mg of hypericin.

* * * * *